US00PP09830P

United States Patent [19]

VandenBerg

[11] Patent Number: Plant 9,830

[45] Date of Patent: Mar. 18, 1997

[54] CHRYSANTHEMUM PLANT NAMED 'SUNNY FARGO'

[75] Inventor: Cornelis P. VandenBerg, Salinas, Calif.

[73] Assignee: Yoder Brothers, Inc., Barberton, Ohio

[21] Appl. No.: 547,659

[22] Filed: Oct. 24, 1995

[51] Int. Cl.[6] ..... A01H 5/00

[52] U.S. Cl. ..... Plt./82.2

[58] Field of Search ..... Plt./82.2

[56] References Cited

U.S. PATENT DOCUMENTS

| | | | |
|---|---|---|---|
| P.P. 9,108 | 4/1995 | VandenBerg | Plt./82.2 |
| 4,616,099 | 10/1986 | Sparkes | 47/58 |

OTHER PUBLICATIONS

Broertjes, et al., 1980, "A mutant of a mutant of a . . . Irradiation of progressive radiation–induced mutants in a mutation breeding programme with *Chrysanthemum morifolium*", Euphytica, 29:525–530.

Gosling, ed., 1979, "The Chrysanthemum Manual—6th edition", The National Chrysanthemum Society, London, Essex Telegraph Press, Ltd., pp. 329–336.

Broertjes, et al., 1978, "Application of Mutation Breeding Methods In the Improvement of Vegetatively Propagated Crops", Elsvier Sci. Publ. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X–rays", Am. Soc. Hort. Sci. Proc., pp. 613–620.

Broertjes, 1966, "Mutation breeding of chrysanthemums", Euphytica, 15:156–162.

Dowrick, et al., 1966, "The induction of mutations in Chrysanthemum using X– and gamma radiation", Euphytica, 15:204–210.

*Primary Examiner*—Howard J. Locker
*Attorney, Agent, or Firm*—Foley & Lardner

[57] ABSTRACT

A Chrysanthemum plant named Sunny Fargo particularly characterized by its flat capitulum form; daisy capitulum type; clear yellow ray floret color; small flowers, with a diameter across face of capitulum of 32 to 38 mm when fully opened, when grown as a single stem spray cut mum; flowering response is 50 to 53 days after start of short days; plant height is 74 to 79 cm when grown with 17 to 18 long days prior to start of short days; peduncle length of the first lateral at flowering after removing he apical bud without growth regulator applications is 5 to 8 cm; peduncle length of the fourth lateral is 8 to 10 cm; terminal spray formation, with the lower laterals being compound; and recommended as spray cut mum.

1 Drawing Sheet

The present invention comprises a new and distinct cultivar of Chrysanthemum, botanically known as *Dendranthema grandiflora,* and referred to by the cultivar name Sunny Fargo.

Sunny Fargo, identified as 0163 (90-547E04), is a product of a mutation induction program. The new cultivar was discovered and selected by inventor Cornelis P. VandenBerg on Sep. 30, 1993 in a controlled environment in Salinas, Calif. as one flowering plant within a flowering block established as rooted cuttings from stock plants which had been exposed as unrooted cuttings to an X-ray source of 1750 rads in Fort Myers, Fla. on Apr. 1, 1993. The irradiated parent cultivar was the cultivar Fargo, disclosed in U.S. Plant patent application, Ser. No. 08/277,285, now U.S. Plant Pat. No. 9,108, and described as a daisy spray cut mum with a yellow ray floret color with a strong bronze overcast of the underside of the ray florets.

The irradiation program resulting in Sunny Fargo had as its primary objective the expansion of color ranges of the parent cultivar Fargo. The irradiation program comprised irradiation of cuttings of the parent cultivar at irradiation levels of 1500, 1750 and 2000 rads. A total of 904 cuttings harvested from a total of 225 irradiated plants were planted on Jul. 19, 1993. Of these, 12 initial selections were made, which selections were then revegetated and reflowered. Three consecutive flowerings in Salinas, Calif. and one flowering in Honselersdijk, The Netherlands, resulted in discarding 9 of the original 12 selections on Sep. 12, 1994. The remaining three selections were maintained as PIs (Possible Introductions) and further trialed in Salinas, Calif. and in Honselersdijk, The Netherlands, ultimately resulting in the decision to introduce two remaining selections as Sunny Fargo and Harvest Fargo. The introduction of Harvest Fargo was delayed because of the need to replace the original Harvest Fargo (code 0166) with remaining selection 0144 Harvest Fargo, because of better uniformity of code 0144. The original code 0166 Harvest Fargo was discarded on May 1, 1995.

The first act of asexual reproduction of Sunny Fargo was accomplished when vegetative cuttings were taken from the initial selection in December of 1993 in a controlled environment in Salinas, Calif., by technicians working under supervision of Cornelis P. VandenBerg.

Horticultural examination of controlled flowerings of successive plantings has shown that the unique combination of characteristics as herein disclosed for Sunny Fargo are firmly fixed and are retained through successive generations of asexual reproduction.

Sunny Fargo has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., under greenhouse conditions which approximate those generally used in commercial greenhouse practice.

The following traits have been repeatedly observed and are determined to be basic characteristics of Sunny Fargo, which, in combination, distinguish this Chrysanthemum as a new and distinct cultivar:

1. Flat capitulum form.
2. Daisy capitulum type.
3. Clear yellow ray floret color.

4. Small flowers, with a diameter across face of capitulum of 32 to 38 mm when fully opened, when grown as a single stem spray cut mum.

5. Flowering response is 50 to 53 days after start of short days.

6. Plant height is 74 to 79 cm when grown with 17 to 18 long days prior to start of short days.

7. Peduncle length of the first lateral at flowering after removing the apical bud without growth regulator applications is 5 to 8 cm; peduncle length of the fourth lateral is 8 to 10 cm.

8. Terminal spray formation, with the lower laterals being compound.

9. Recommeded as spray cut mum.

The accompanying photographic drawing is a side view of a single stem cut spray mum of Sunny Fargo, with the colors being as nearly true as possible with illustrations of this type.

Of the commercial cultivars known to the inventor, the most similar in comparison to Sunny Fargo is the parent cultivar Fargo. All traits of Sunny Fargo are similar to those of Fargo, except for the ray floret color. The ray floret color of Sunny Fargo is clear yellow, while the ray floret color of Fargo is yellow with a strong bronze overcast of the underside of the ray florets.

In the following description color references are made to The Royal Horticultural Society Colour Chart. The color values were determined on plant material grown as a single stem spray cut mum grown in Salinas, Calif. on Jun. 27, 1995.

Classification:

*Botanical.*—*Dendranthema grandiflora* cv Sunny Fargo.

*Commercial.*—Flat daisy spray cut mum.

INFLORESCENCE

A. Capitulum:
- *Form.*—Flat
- *Type.*—Daisy.
- *Diameter across face.*—32 to 38 mm when fully opened.

B. Corolla of ray florets:
- *Color (general tonality from a distance of three meters).*—Yellow.
- *Color (upper surface).*—12A.
- *Color (under surface).*—12B.
- *Shape.*—Straight, flat, slightly pointed.

C. Corolla of disc florets:
- *Color (mature).*—14A.
- *Color (immature).*—144B.

D. Reproductive organs:
- *Androecium.*—Present on disc florets only; no pollen.
- *Gynoecium.*—Present on both ray and disc florets.

PLANT

A. General appearance:
- *Height.*—74 to 79 cm when grown in Salinas with 17 to 18 long days prior to start of short days.

B. Foliage:
- *Color* (upper surface).—147A.
- *Color (under surface).*—147B.
- *Shape.*—Deeply lobed, serrated.

What is claimed:

1. A new and distinct Chrysanthemum plant named Sunny Fargo, as described and illustrated.

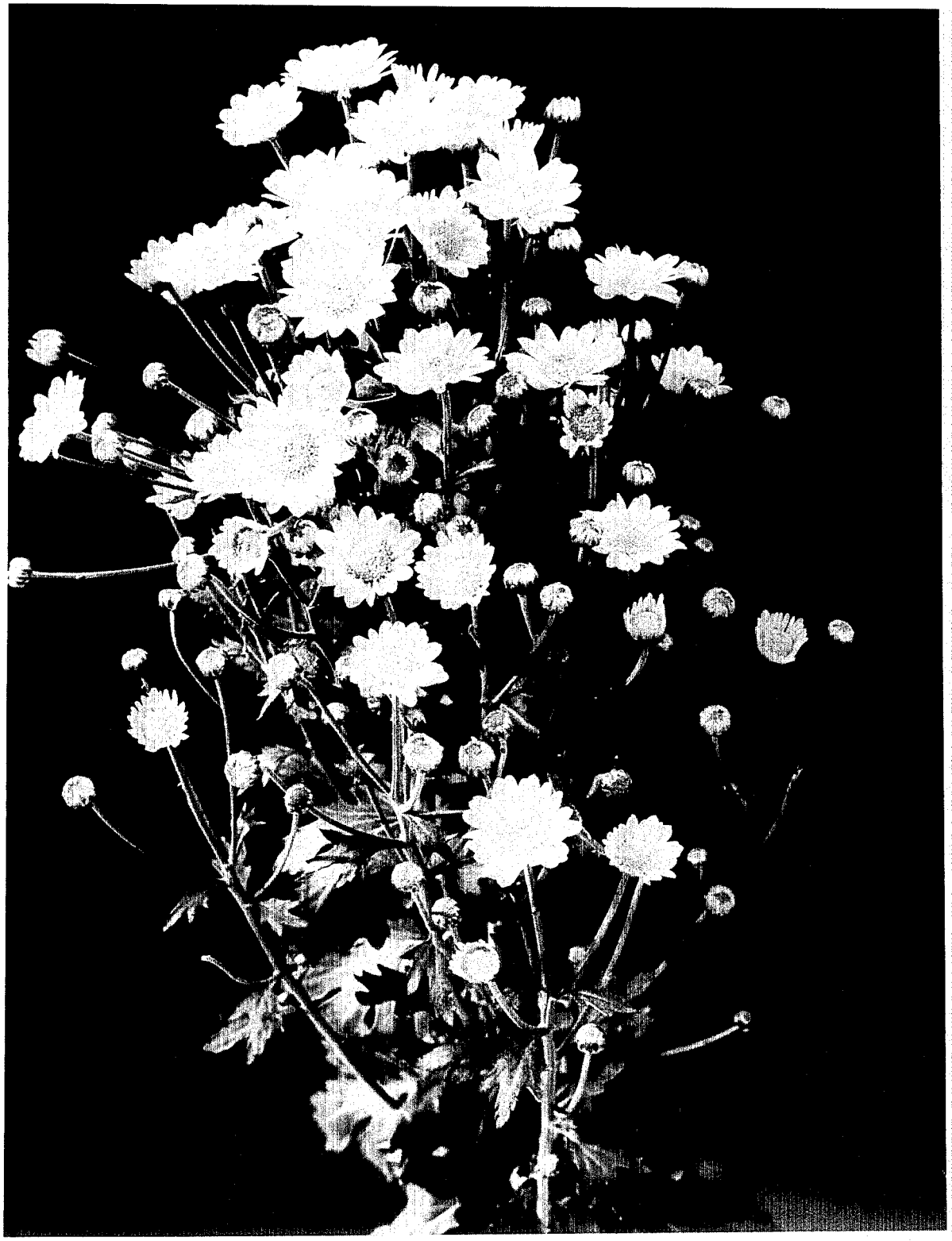

* * * * *